United States Patent [19]

Mikkelsen

[11] Plant 5,131

[45] Nov. 1, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,078

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Solared and characterized by its brilliant scarlet flowers; high floriferousness; early blooming and continuous flowering with frost; superior self-branching and compact; mounded growth habit; variegated dark green foliage; resistance to fading; and by its adaptability to various use environments.

1 Drawing Figure

1

The present invention relates to a new and distinct cultivar of Impatiens plant, botanically known as Impatiens and known by the cultivar name Solared. The new cultivar was developed by me through controlled breeding in Ashtabula, Ohio. The seed parent was 79-1183-6 (Mikkelsen), and the pollen parent was 79-1316-2 (Mikkelsen). Asexual reproduction of terminal or stem cuttings has shown that the unique features of this new impatiens are stabilized and are reproduced true to type in successive propagations.

The following characteristics distinguish Solored from both its parent varieties and other cultivated impatiens of this type known and used in the floriculture industry:

1. Brilliant luminescent scarlet (orange/red) flowers. Flower color is lighter than flowers of Red Planet, disclosed in U.S. Plant Pat. No. 4,690, or Flare, disclosed in my pending application.
2. The new cultivar is more floriferous than Red Planet or Flare. Flower size is comparable to Red Planet but slightly smaller than Flare.
3. The new cultivar is self-branching, very compact, mounded, low growing.
4. The type of growth allows the plant to be used for pots of small flowering plants, hanging baskets, mass displays, or single plants for accent in the garden.
5. Solared blooms early and continues floriferous blooming outside during the entire summer until killing frost.
6. Nicely variegated dark green foliage maintains good quality throughout the outdoor growing season. Variegation is more distinct than Flare but not as dominant as in Red Planet.
7. A light pink ring develops at the base of the petals and varies in diameter around the ovary. Wind damage to flower petals is noticeable as damaged areas turn white.
8. Besides the outstanding flower color, there is a very distinctive pleasing contrast between flower color and the variegated color of the leaves, as illustrated in the photograph.
9. Of the three outstanding red cultivars Red Planet, Flare, and Solared, uniform flower color is maintained in the highest degree in Solared.

The accompanying colored photograph taken in mid-August in full sun illustrates the overall appearance of Solared. The photo is a generally top perspective view of the plant, and shows the colors outside as true as it is

2 reasonably possible to obtain in a colored reproduction of this type.

The following is a detailed description of my new impatiens cultivar based on plants produced under commercial practice in Ashtabula, Ohio. The illustrated specimen was planted outside in full sun the second week of June from a 4" pot. The picture was taken mid-August showing the plant 45 cm. in diameter×25 cm. high. Flowering continued until killing frost in early November. Color references are made to the Royal Horticultural Society Colour Chart except where general terms of ordinary dictionary significance are used.

Parentage: Mikkelsen seedling 79-1183-6 crossed with Mikkelsen seedling 79-1316-2.

Propagation:

(A) *Stem cuttings.*—Cuttings 15 mm. long will develop to 4–5 cm. in 21–28 days.

(B) *Time to initiate root.*—8–10 days at 23° C. summer.

(C) *Time to initiate root.* 12–14 days at 20° C. winter.

(C) *Rooting habit.*—Very fibrous, dendritic, abundant.

Plant description:

(A) *Form.*—Low, compact, red stems self-branching, symmetrically mounded, early flowering herb.

(B) *Habit of growth.*—Medium rate of growth, close internodes, self-branching, vigorous stems with excellent foliage retention.

(C) *Foliage.*—Dark green leaves, strongly variegated, concave, opposite on vegetative shoots, developing into a whorl of 6–7 leaves when flowering occurs. (1) Size: 8–10 cm. long×3.5 cm. wide (flattened out). (2) Shape: Lanceolate, apex acuminate, base acute. (3) Texture: Top rugose, underside glabrous. (4) Margin: Finely serrated. (b 5) Color: Young foliage, top side yellow green 147-A; under side yellow green 147-B. Mature foliage, top side green 139-A; underside green 137-B. Basal and mid-rib area highly variegated, cream to yellow. (6) Venation: Pinnate.

Flowering description:

(A) *Flowering habits.*—Flowering occurs year around with flowers developing from a whorl of leaves, usually one flower per leaf. Flowering develops one at a time around the whorl with last flowers still in bloom as first flowers open at the next whorl.

(B) *Natural flowering season.*—Indeterminate and year around, with the amount and speed of flowering dependent on quantity of light.

(C) *Flower buds.*—Ellipsoidal, flowers perfect, dark red spur with throat originating from dominant sepal and elongating up to 5 cm.

(D) *Flowers borne.*—Short pedicel originating from base of leaf, flowers are close to foliage, 6–7 buds bloom progressively around leaf whorl.

(E) *Quantity of flowers.*—Close internodes and rapid self-branching gives appearance of being highly floriferous.

(F) *Petals.*—(1) Shape: Heart-shaped, apex slightly indented, top petal largest; other four equal. (2) Color, top side when opening luminescent scarlet red 40-B in winter, 42-B full sun in summer, with little fading by age; difference in color only during different seasons; under side lighter, 42-C. (3) Number of petals: Five (5). (4) Size of flowers: 4.5 cm. to 5 cm.

(G) *Reproductive organs.*—(1) Stamens: Five (5) in number. (a) Another shape: Hooded, color red. (b) Pollen color: Cream. (2) Pistils: (a) Stigma: Five (5) in number, segmented column-shaped; clear. (b) Style color: Clear. (c) Ovaries: Five (5) celled, size 6 mm. long before fertilization, green in color. Capsule explosively dehiscent.

Disease resistance: Since origination of the cultivar to date there has been no apparent problems with serious diseases or insects other than botrytis petal rot under adverse weather conditions.

I claim:

1. A new and distinct cultivar of impatiens plant, known by the cultivar name Solared, as described and illustrated, and particularly characterized as to uniqueness by its brilliant scarlet flowers, high floriferousness, early blooming and continuous flowering until frost, superior self-branching and compact, mounded growth habit, variegated dark green foliage, resistance to fading, and by its adaptability to various use environments.

* * * * *

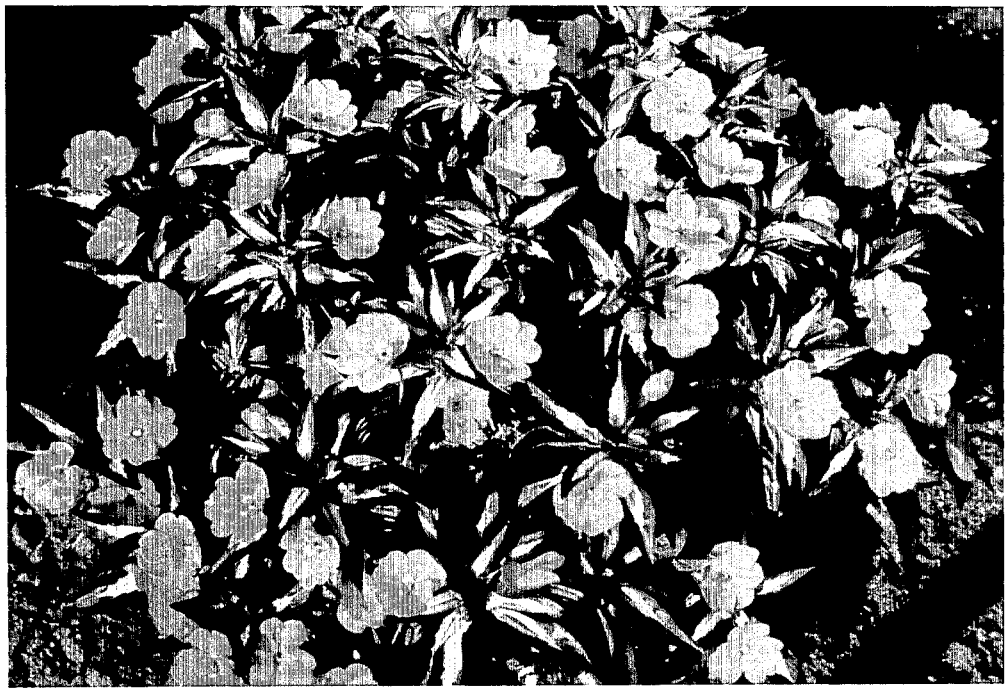

UNITED STATES PATENT AND TRADEMARK OFFICE

CERTIFICATE OF CORRECTION

PATENT NO. :PP 5131

DATED :November 1, 1983

INVENTOR(S) : JAMES C. MIKKELSEN

It is certified that error appears in the above—identified patent and that said Letters Patent is hereby corrected as shown below:

The color photographic drawing appearing with this plant patent should be the color photographic drawing as shown per attached.

Signed and Sealed this

*Eleventh* Day of *September 1984*

[SEAL]

*Attest:*

GERALD J. MOSSINGHOFF

*Attesting Officer*

*Commissioner of Patents and Trademarks*